(12) United States Patent
Yamaguchi et al.

(10) Patent No.: US 7,527,379 B2
(45) Date of Patent: May 5, 2009

(54) OPHTHALMOLOGIC IMAGING APPARATUS

(75) Inventors: Tatsuo Yamaguchi, Tokyo (JP);
Toshifumi Mihashi, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 11/812,089

(22) Filed: Jun. 14, 2007

(65) Prior Publication Data

US 2007/0291229 A1 Dec. 20, 2007

(30) Foreign Application Priority Data

Jun. 16, 2006 (JP) .............................. 2006-167233

(51) Int. Cl.
*A61B 3/10* (2006.01)
(52) U.S. Cl. ..................................... 351/205; 351/221
(58) Field of Classification Search ................. 351/205, 351/221
See application file for complete search history.

(56) References Cited

U.S. PATENT DOCUMENTS

| 6,550,917 | B1* | 4/2003 | Neal et al. .................. 351/221 |
| 6,685,650 | B2 | 2/2004 | Tanaka |
| 6,890,076 | B2 | 5/2005 | Roorda |
| 7,270,415 | B2* | 9/2007 | Yamaguchi et al. ......... 351/221 |
| 2005/0219461 | A1* | 10/2005 | Hirohara ..................... 351/205 |

FOREIGN PATENT DOCUMENTS

| JP | 2004-113405 A | 4/2004 |
| JP | 2004-159779 A | 6/2004 |
| JP | 2004-159784 A | 6/2004 |
| JP | 2004-329282 A | 11/2004 |
| JP | 2006-006362 A | 1/2006 |

OTHER PUBLICATIONS

U.S. Appl. No. 11/812,092, filed Jun. 14, 2007, Yamaguchi et al.
T. Yamaguchi, U.S. PTO Office Action, U.S. Appl. No. 11/812,092, May 8, 2008, 19 pages.
T. Yamaguchi, U.S. PTO Notice of Allowance and Fee(s) Due, U.S. Appl. No. 11/812,092, Jan. 5, 2009, 8 pages.

\* cited by examiner

*Primary Examiner*—Ricky L Mack
*Assistant Examiner*—Dawayne A Pinkney
(74) *Attorney, Agent, or Firm*—Foley & Lardner LLP

(57) ABSTRACT

A first wavelength for measurement is selected from among a plurality of wavelengths. Aberrations at the first wavelength are measured with a wavefront-measurement light source having the first wavelength. A compensation optical section performs compensation so as to cancel out the measured aberrations. After the compensation, a retinal image is obtained from a retina imaging device using a retina illumination light source having the same wavelength as the wavefront-measurement light source. During image-data transfer from the retina imaging device, aberrations at a second wavelength are measured using another wavefront-measurement light source having the second wavelength. The compensation optical section performs compensation so as to cancel out the measured aberrations. After the compensation, a retinal image is obtained using another retina illumination light source having the same wavelength as the another wavefront-measurement light source. A difference image is obtained from the retinal images, and displayed or stored.

10 Claims, 10 Drawing Sheets

FIG.4 TIMING CHART

IMAGE OBTAINED WITH WAVELENGTH B (IN MEMORY MB)

DIFFERENCE IMAGE

IT IS UNDERSTOOD BY SPECTROSCOPIC MEASUREMENT THAT CELLS REACT DIFFERENTLY

IMAGE OBTAINED WITH WAVELENGTH A (IN MEMORY MA)

EXAMPLE FOR USING THREE LIGHT SOURCES

OPHTHALMOLOGIC IMAGING APPARATUS

This application claims priority from Japanese Patent Application No. 2006-167233, filed Jun. 16, 2006, which is incorporated herein by reference in its entirety.

BACKGROUND OF THE INVENTION

1. Field of the Invention

The present invention relates to ophthalmologic imaging apparatuses, and more particularly, to an ophthalmologic imaging apparatus for obtaining retinal images at a high magnification within a short period of time with light beams having different wavelengths.

2. Description of the Related Art

The following technologies have been disclosed by the assignee of present application. An eye-characteristic measurement apparatus which compensates for aberrations of an eye under measurement by a compensation optical section and measures precisely a minute aberration remaining after compensation is disclosed, for example, in Japanese Unexamined Patent Application Publication No. 2004-113405, No. 2004-159779, and No. 2004-159784. A retina observation apparatus which compensates a light beam reflected by an eye under measurement in order to improve retina-image quality and obtains an optimal image is disclosed, for example, in Japanese Unexamined Patent Application Publication No. 2004-329282. A retina-image observation apparatus which detects a displacement of an eye under measurement and moves a wavefront compensation device according to the detected shift position to compensate the wavefront is disclosed, for example, in Japanese Unexamined Patent Application Publication No. 2006-006362.

To obtain images with two or more light beams having different wavelengths in a conventional ophthalmologic imaging apparatus, the light source is switched or another apparatus is used.

To compare or combine images obtained with two or more light beams having different wavelengths in a conventional ophthalmologic imaging apparatus, however, it would be necessary to perform image compensation to conduct comparison because the imaging position and the focusing position lack reproducibility. In addition, fundamentally, since the wavelength of light emitted from a light source used to measure wavefront aberration is different from that of light emitted from a light source used to observe a retina, there is a case that chromatic aberration cannot be removed by a compensation optical section and others, so that image quality deteriorates in some cases. If the wavefront-measurement light source and the retina illuminating light source emit light beams having the same wavelength, a light beam for a wavefront measurement system would affect an imaging device for retinal images, as noise, to reduce the signal-to-noise ratio (S/N) in some cases.

SUMMARY OF THE INVENTION

Accordingly, it is an object of the present invention to provide an ophthalmologic imaging apparatus for obtaining quality images within a short period of time with a plurality of light beams having different wavelengths. Another object of the present invention is to provide an ophthalmologic imaging apparatus for synchronizing and controlling a wavefront measurement light source, a retina illumination light source, an imaging device for retinal images, and a wavefront compensation device according to the measured state of wavefront aberration. Still another object of the present invention is to compare oxygen saturation by the comparison of retinal images and to display in detail the state of a retina in a diversified manner in color, enabled by combining images.

According to the solving means of this invention, there is provided an ophthalmologic imaging apparatus comprising:

a first light source section comprising a first light source for emitting a light beam having a first wavelength and a second light source for emitting a light beam having a second wavelength both for illuminating a desired observation area on a retina of an eye under measurement;

a second light source section comprising a third light source for projecting a light beam having the first wavelength on the retina as an almost point image and a fourth light source for projecting a light beam having the second wavelength on the retina as an almost point image;

a first illumination optical system for illuminating the observation area on the retina, with a first light beam emitted from the first light source section;

a second illumination optical system for projecting a second light beam emitted from the second light source section on the retina as an almost point image;

an aberration compensation section for applying compensation to a first reflected light beam obtained when the first light beam is reflected by the retina and a second reflected light beam obtained when the second light beam is reflected by the retina so as to cancel out aberrations that include at least high-order aberrations, according to aberrations measured at the first wavelength and the second wavelength;

an aberration measurement section comprising a second light-receiving section for receiving the second reflected light beam which aberrations have been compensated for by the aberration compensation section, through a dividing means for dividing into at least 17 beams, the aberration measurement section measuring aberrations of the second reflected light beam at the first wavelength or the second wavelength according to a light-receiving signal of the second light-receiving section;

a first light-receiving section for receiving the first reflected light beam coming from the retina, for which aberrations have been compensated for by the aberration compensation section; and a light-receiving optical system for forming a retinal image on the first light-receiving section with the first reflected light beam coming from the retina through the aberration compensation section, wherein, after a light beam is emitted from the third light source and aberrations at the first wavelength are compensated for by the aberration compensation section, a first retinal image formed through the aberration compensation section on the first light-receiving section by a light beam coming from the first light source is obtained; and after a light beam is emitted from the fourth light source and aberrations at the second wavelength are compensated for by the aberration compensation section, a second retinal image formed through the aberration compensation section on the first light-receiving section by a light beam coming from the second light source is obtained.

According to the present invention, it can provide an ophthalmologic imaging apparatus for obtaining quality images within a short period of time with a plurality of light beams having different wavelengths. According to the present invention, it can provide an ophthalmologic imaging apparatus for synchronizing and controlling a wavefront measurement light source, a retina illumination light source, an imaging device for retinal images, and a wavefront compensation device according to the measured state of wavefront aberration. According to the present invention, it can compare oxygen saturation by the comparison of retinal images and display in detail the state of a retina in a diversified manner in color, enabled by combining images.

DESCRIPTION OF THE PREFERRED EMBODIMENTS

1. Outline

The present embodiment relates to an adaptive optics apparatus that allows spectrometric measurement for each selected wavelength. In the present embodiment, when light sources emit several pulse light beams having different wavelengths, for example, sequentially to an eye under measurement, spectroscopic retinal images can be obtained within a very short period of time. When a light source for wavefront measurement is used during a transfer period of an imaging device for retinal images, noise caused by the light source for wavefront measurement is prevented from affecting obtained retinal images. In addition, retinal images taken at a high magnification with two light beams having different wavelengths are compared to find many aspects such as the activity level of the retina and the distributions of L and M cone cells. If the light sources emit light beams having wavelengths corresponding to three primary colors, such as red, green, and blue, a color image can also be obtained.

2. Optical Arrangement

Figure 1:
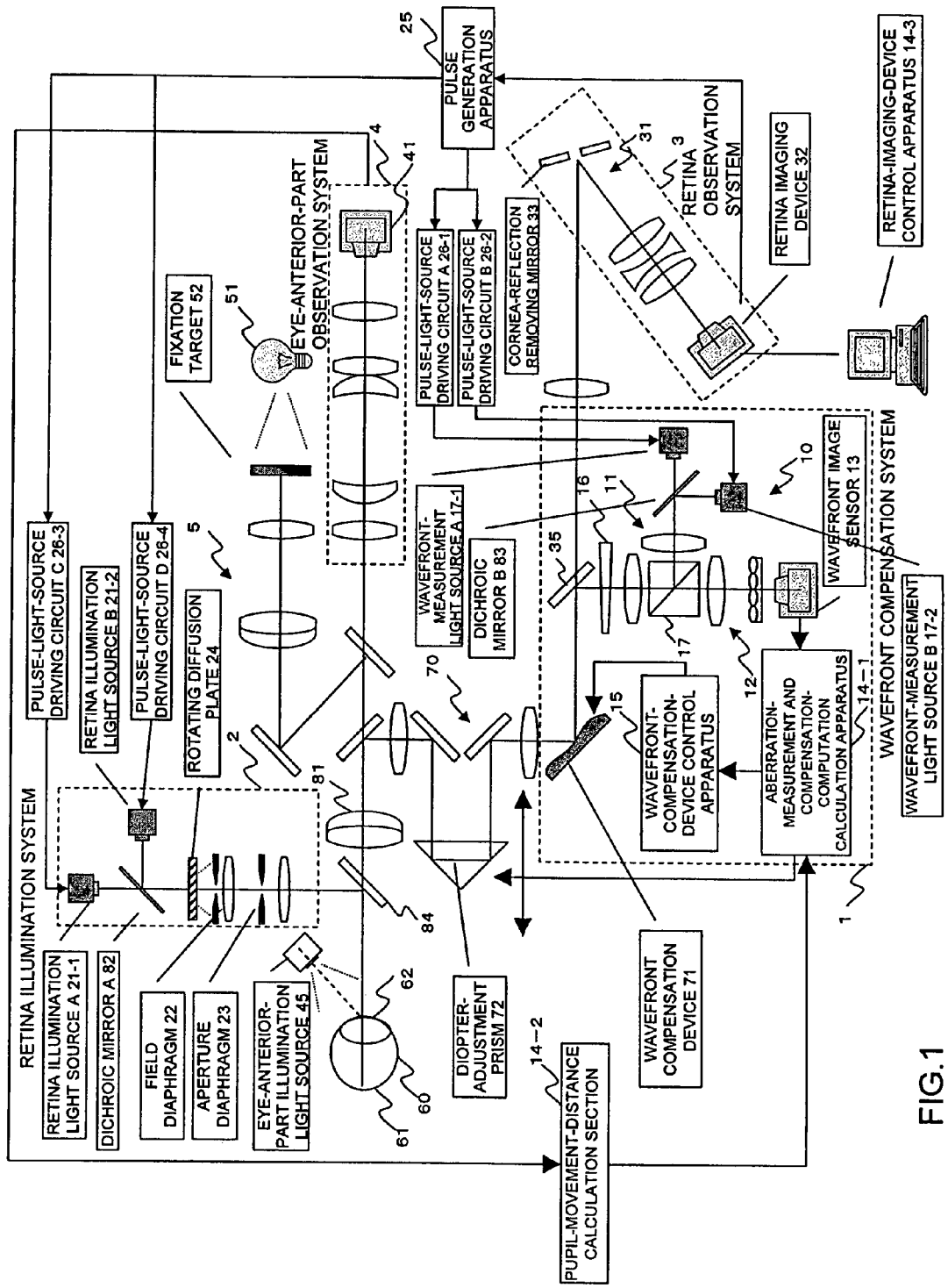
FIG. 1 is a view showing the optical arrangement of an embodiment.

FIG. 1 is a view showing the optical arrangement of the present embodiment.

A retina observation apparatus (ophthalmologic imaging apparatus) includes a wavefront compensation system 1, a retina illumination system (first illumination optical system) 2, a retina observation system 3, an eye-anterior-part observation system 4, an eye-anterior-part illumination light source 45, a fixation system 5, a compensation optical section 70, a pupil-movement-distance calculation section 14-2, a retina-imaging-device control apparatus (retinal-image generation section) 14-3, a pulse generation apparatus 25, and a plurality of pulse-light-source driving circuits 26. The plurality of pulse-light-source driving circuits 26 includes, for example, a pulse-light-source driving circuit A 26-1, a pulse-light-source driving circuit B 26-2, a pulse-light-source driving circuit C 26-3, and a pulse-light-source driving circuit D 26-4.

The wavefront compensation system (aberration measurement section) 1 includes a wavefront measurement system 10 having a second illumination optical system 11, a second light-receiving optical system 12 and a second light-receiving section 13, an aberration-measurement and compensation-computation calculation apparatus (aberration calculation section, hereinafter called a calculation apparatus) 14-1, a wavefront-compensation-device control apparatus 15, and a dichroic mirror B 83. The calculation apparatus 14-1, the pupil-movement-distance calculation section 14-2, and the retinal-image generation section 14-3 can, for example, be provided for one calculation section or a plurality of calculation sections. In the figure, a retina (eyeground) 61 and a cornea (eye anterior part) 62 are shown in the eye under measurement 60.

The second illumination optical system (point-image projection optical system) 11 includes, for example, a second light source section (for example, a first wavefront-measurement light source A 17-1 and a second wavefront-measurement light source B 17-2), and illuminates a minute area (or a target) on the retina of the eye under measurement by light beams emitted from the first wavefront-measurement light source A 17-1 and the second wavefront-measurement light source B 17-2. The second illumination optical system 11 also includes, for example, a condenser lens and a relay lens.

It is preferred that the first wavefront-measurement light source A 17-1 and the second wavefront-measurement light source B 17-2 have high spatial coherence and not-high temporal coherence. As an example case, a laser diode (for example, having a first wavelength of 532 nm) can be used as the first wavefront-measurement light source A 17-1 and a laser diode (for example, having a second wavelength of 635 nm) can be used as the second wavefront-measurement light source B 17-2. When high-coherent light sources, such as laser diodes, are used as the first wavefront-measurement light source A 17-1 and the second wavefront-measurement light source B 17-2, the coherence may be reduced by rotating a diffusion plate at a high speed to reduce speckles. Light sources having not-high spatial coherence and not-high temporal coherence, such as LEDs, can be used if the amount of light emitted is sufficient and a pinhole is inserted in the optical path at the position of each light source.

As the dichroic mirror B 83, a hot mirror that reflects light having the second wavelength (for example, 635 nm) and passes light having the first wavelength (for example, 532 nm) can be used.

The second light-receiving optical system (point image light-receiving optical system) 12 receives light reflected by and returned from the retina and guides it to the first light-receiving section (such as a wavefront image sensor) 13. The second light-receiving optical system 12 includes a relay lens, a beam splitter, and a conversion member (a splitting device such as a Hartman plate) for converting the reflected light beam into at least 17 beams. The beam splitter 17 is formed of a mirror (such as a polarization beam splitter) which reflects light emitted from the first wavefront-measurement light source A 17-1 and the second wavefront-measurement light source B 17-2 and transmits the reflected light beam reflected by the retina of the eye under measurement 60 and returned through an afocal lens 81. The conversion member is a wavefront conversion member for converting the reflected light beam into a plurality of beams. A plurality of micro Fresnel lenses disposed on a plane perpendicular to the optical axis can be used as the conversion member. The light beam reflected from the retina 61 is condensed on the first light-receiving section 13 through the conversion member.

The second light-receiving section 13 receives light from the second light-receiving optical system 12, which is transmitted through the conversion member, and generates a first signal.

While the second illumination optical system 11 and the second light-receiving optical system 12 keep a relationship such that, assuming that light emitted from the first wavefront-measurement light source A 17-1 and the second wavefront-measurement light source B 17-2 is reflected at a point where the light is condensed, the second light-receiving section 13 has the maximum signal peak of the reflected light, a prism 72 can be moved in a direction in which the signal peak obtained by the second light-receiving section 13 increases and stopped at a position where the signal peak reaches the maximum. As a result, the light emitted from the first wavefront-measurement light source A 17-1 and the second wavefront-measurement light source B 17-2 is condensed on the eye under measurement.

The first illumination optical system (retina illumination system) 2 includes, for example, a first light source section (for example, a first retina illumination light source A 21-1 and a second retina illumination light source B 21-2), a field diaphragm 22, an aperture diaphragm 23, a rotating diffusion plate 24, a dichroic mirror A 82, a condenser lens, and a beam splitter 84, and illuminates a predetermined region on the retina (eyeground) of the eye under measurement with first light beams coming from the first retina illumination light source A 21-1 and the second retina illumination light source B 21-2.

As the first retina illumination light source A 21-1, for example, a laser diode emitting light having the same first wavelength (for example, 532 nm) as that of light emitted by the first wavefront-measurement light source A 17-1 can be used. As the second retina illumination light source B 21-2, a laser diode emitting light having the same second wavelength (for example, 635 nm) as that of light emitted by the second wavefront-measurement light source B 17-2 can be used. The pulse width preferably falls in a range of several picoseconds to several hundreds of microseconds. When the frame rate of an imaging device 32 is low (about 10 Hz), it is preferable that short pulses be output during data transfer in order to prevent photosensitive epilepsy. As the dichroic mirror A 82, the same mirror as that used for the above-described dichroic mirror B 83 can be used. The beam splitter 84 can, for example, be a beam splitter that reflects light beams coming from the first retina illumination light source A 21-1 and the second retina illumination light source B 21-2 and passes a light beam reflected back from the eye under measurement 60.

As shown in FIG. 1, light is incident from the inside of the pupil and a plate (such as a mirror with an opening used in the figure) which blocks light is inserted at a conjugate point with the cornea and the crystalline lens, so that noise (uninvited reflection) caused by the cornea and others can be removed. The aperture diaphragm 23 of the first illuminating optical system 2 can be disposed close to a conjugate point with the pupil to make an optical system which removes noise light by a cornea-reflection removing mirror, described later. The viewing-field diaphragm 22 is disposed at a conjugate point with the retina. With this, light can be concentrated on an area where cells are observed, and a load imposed on the person under measurement can be reduced.

When a mirror with an opening is used, the mirror with the opening and the pupil are made to have a conjugate relationship or in the vicinity in order to prevent reflection at a vertex of the cornea. A ring-shaped aperture may also be used when the center thereof has a transmittance of 100%, surroundings of the center have a transmittance of about 10%, and light transmitting the surroundings illuminates the whole of the retina 61.

The rotating diffusion plate 24 reduces speckles of a high-coherence light source (for example, a pulse laser) when being rotated at high speed. Although it depends on the exposure period, it is preferable that the plate be rotated at a rotation speed of about 10,000 rpm or more. The pulse generation apparatus 25 generates pulses in synchronization with exposure signals sent from the retinal image sensor 32 and the wavefront image sensor 13. When a very fast pulse laser is used such as a picosecond laser, pulses are generated during exposure. The pulse generation apparatus 25 sends the generated signals (pulses) to the pulse-light-source driving circuit A 26-1 to the pulse-light-source driving circuit D 26-4. The pulse-light-source driving circuit A 26-1 to the pulse-light-source driving circuit D 26-4 drive the first wavefront-measurement light source A 17-1, the second wavefront-measurement light source B 17-2, the first retina illumination light source A 21-1, and the second retina illumination light source B 21-2 according to the signals input from the pulse generation apparatus 25 to emit light according to the pulses.

The retina observation system 3 includes a first light-receiving optical system 31 and the first light-receiving section (such as a retina imaging device or retinal image sensor) 32. The first light-receiving optical system (retinal-image-generation optical system) 31 includes, for example, an afocal lens 81, a half mirror 35, a condenser lens, and a cornea-reflection removing mirror 33, and guides light having the first and second wavelengths reflected from the retina 61 to the first light-receiving section 32 through the compensation optical section 70. The first light-receiving section 32 receives a retinal image generated by the first light-receiving optical system 31 and generates a second signal. The half mirror 35 divides a light beam reflected from the eye under measurement into two light beams and guides them respectively to the first light-receiving optical system 31 and to the second light-receiving optical system 12.

The cornea-reflection removing mirror 33 is preferably used at a small angle in order to make the pupil conjugate. Using an optical system like a second retina observation system, described later, is an effective way. In the present embodiment, the afocal lens 81, the half mirror 35, and others are provided for the second light-receiving optical system 31 for convenience. They may be provided for the first light-receiving optical system 12.

The compensation optical section (aberration compensation section) 70 has a wavefront compensation device 71 such as adaptive optical system (adaptive optics) for compensating measurement light for aberration, the moving prism (diopter-adjustment prism) 72 for moving along the optical axis to compensate a spherical component and/or a spherical lens. The compensation optical section 70 is disposed in the first and second light-receiving optical systems 12 and 31, and compensates, for example, for the aberrations (including higher-order aberrations) of a reflected light beam reflected by and returned from the eye under measurement 60. The compensation optical section 70 may compensate light emitted from the first wavefront-measurement light source A 17-1 and the second wavefront-measurement light source B 17-2 for aberration to illuminate a minute area on the retina of the eye under measurement by a light beam of which aberration has been compensated for.

The wavefront compensation device 71 can be a variable-shape mirror (a deformable mirror or a variable mirror) or a spatial light modulator such as liquid crystal. An appropriate optical system capable of compensating measurement light for aberration may also be used. A variable-shape mirror changes the reflection direction of light by deforming the mirror by an actuator provided inside the mirror. Other appropriate deforming methods can be used such as a deforming method using a capacitor or a piezoelectric device. A liquid-crystal spatial light modulator uses a liquid-crystal alignment characteristic to modulate a phase, and is used in reflection in many cases in the same way as the variable-shape mirror. When the liquid-crystal spatial light modulator is used, a polarizer is required in an optical path in some cases. The wavefront compensation device 71 may be a transmission-type optical system, in addition to a reflection-type optical system. The wavefront compensation device 71 compensates for aberration by, for example, being deformed according to the output of the wavefront-compensation-device control apparatus 15.

It is preferred that a parallel light beam be incident on the wavefront compensation device 71. Incident light is not limited to parallel light beams. When the eye under measurement 60 has no aberration, for example, light reflected from the retina of the eye under measurement 60 is incident on the wavefront compensation device 71 as a parallel light beam. Light emitted from the first wavefront-measurement light source A 17-1 and the second wavefront-measurement light source B 17-2 are incident on the wavefront compensation device 71 as a parallel light beam.

The moving prism 72 is moved according to the output of the calculation apparatus 14-1. The moving prism 72 is driven, for example, by an appropriate driving section. A spherical component can be compensated for because the moving prism 72 is moved. The spherical component can be compensated for if a spherical lens is used, instead of moving the moving prism 72.

A motored stage that moves the wavefront compensation device 71 according to the output of a motor control circuit by following the pupil movement distance obtained by the pupil-movement-distance calculation section 14-2 can be further provided. For example, the motored stage moves the wavefront compensation device 71 in a direction traversing the optical axis or in a plane perpendicular to the normal line. With this, a point (such as the center) of the wavefront compensation device 71 always becomes conjugate with a point (such as the pupil center) of the pupil, allowing stable wavefront compensation.

The eye-anterior-part illumination light source 45 illuminates an eye anterior part of the eye under measurement 60. For example, a Placido's ring or a keratoring may be used to project a predetermined pattern on the eye anterior part. When a keratoring is used, a pattern just around the center of curvature of the cornea is obtained by a keratoimage. The wavelength of light emitted from the eye-anterior-part illumination light source 45 is, for example, different from the first wavelength and the second wavelength (532 nm and 635 nm in this case), and can be a long wavelength (such as 940 nm).

The eye-anterior-part observation system 4 includes a condenser lens and an eye-anterior-part image sensor 41, and guides a light beam emitted from the eye-anterior-part illumination light source 45 and reflected by and returned from the cornea 62 of the eye under measurement 60, to the eye-anterior-part image sensor 41. As a light source section, an appropriate light source for illuminating the eye under measurement 60 may be used instead of the eye-anterior-part illumination light source 45. The eye-anterior-part observation system 4 can also guide a light beam reflected by and returned from the eye anterior part or the cornea 62 of the eye under measurement 60 when an appropriate pattern (such as a Placido's ring) is projected on the eye under measurement 60, to the eye-anterior-part image sensor 41. The eye-anterior-part image sensor 41 can obtain an eye-anterior-part image. The eye-anterior-part observation system 4 can also be used for alignment. The wavelength of light used for alignment can be a long wavelength (such as 940 nm) different, for example, from the first wavelength and the second wavelength (532 nm and 635 nm in this case).

The third illumination optical system (fixation system) 5 includes, for example, an optical path for projecting an eyesight-target for making the eye under measurement 60 have fixation or clouding and fogging, and is provided with a third light source section (such as a lamp) 51, a fixation target 52, and a relay lens. The system 5 can project the fixation target 52 on the retina 61 with a light beam emitted from the third light source section 51, and makes the eye under measurement 60 observe its image.

The wavefront-compensation-device control apparatus 15 deforms the wavefront compensation device 71 according to the output of the calculation apparatus 14-1. For example, the wavefront-compensation-device control apparatus 15 generates a control signal (such as a voltage) for deforming each element of the wavefront compensation device 71, based on wavefront aberration measured by the calculation apparatus 14-1 or based on compensation obtained by the calculation apparatus 14-1, and outputs the generated control signal to the wavefront compensation device 71 to compensate the wavefront.

The calculation apparatus 14-1 obtains optical characteristics that includes higher-order aberrations, of the eye under measurement 60 or of a light beam which was reflected by the eye under measurement 60 and of which aberrations have been compensated for by the compensation optical section 70, according to the output from the second light-receiving section 13. The calculation apparatus 14-1 may receive, instead of the output from the first light-receiving section 13, wavefront measurement data that indicates at least the wavefront aberration of the eye under measurement 60 to obtain the optical characteristics. The calculation apparatus 14-1 also determines the amount of compensation for the wavefront compensation device 71 according to the obtained optical characteristics and outputs the amount of compensation to the wavefront-compensation-device control apparatus 15.

The pupil-movement-distance calculation section 14-2 measures the displacement of the eye under measurement (such as the movement distance of the pupil) from the eye-anterior-part image generated by the eye-anterior-part image sensor 41. The pupil-movement-distance calculation section 14-2 can measure the movement distance of the center of the pupil as the displacement of the eye under measurement, but it may also obtain the movement distance of an appropriate position of the eye under measurement, such as the vertex of the cornea. The fundus-image generation section 14-3 obtains an fundus-image generated by the second light-receiving section 32, and displays or outputs the fundus-image.

Conjugate Relationship

The retina 61 of the eye under measurement 60, the fixation target 52 in the fixation system 5, the first wavefront-measurement light source A 17-1 and the second wavefront-measurement light source B 17-2, and the second light-receiving section 13 are conjugate. The pupil (iris) of the eye under measurement 60 and the conversion member (Hartman plate) of the first light-receiving optical system 12 are conjugate. The rotating diffusion plate 24 is conjugate with the pupil (an image is formed on the pupil), and can uniformly illuminate the whole of most of the retina 61.

Alignment Adjustment

Alignment adjustment will next be described. Alignment adjustment can be performed, for example, by the eye-anterior-part observation system 4.

Since an image of the eye under measurement 60 is formed on the eye-anterior-part image sensor 41 by the eye-anterior-part illumination light source 45 (light source section), which illuminates the cornea 62 of the eye under measurement 60, alignment adjustment needs to be performed such that the center of the pupil matches the optical axis by using the image of the eye under measurement 60.

When a light source for illuminating the eye under measurement 60 by parallel light beams through the condenser lens, the beam splitter, and the afocal lens 81 is added to the eye-anterior-part observation system 4, light beams reflected by the cornea 62 of the eye under measurement 60 are returned as if they were diverging from a point positioned at half the radius of curvature of the cornea 62. The diverging light beams pass through the afocal lens 81, the beam splitter, and the condenser lens, and the eye-anterior-part image sensor 41 receives the light beams as a spot image. If the spot image on the eye-anterior-part image sensor 41 is not on the optical axis, the retina observation apparatus is moved up and down and from side to side so that the spot image is on the optical axis. When the spot image is brought onto the optical axis, alignment adjustment is completed.

3. Electrical-system Configuration

Figure 2:
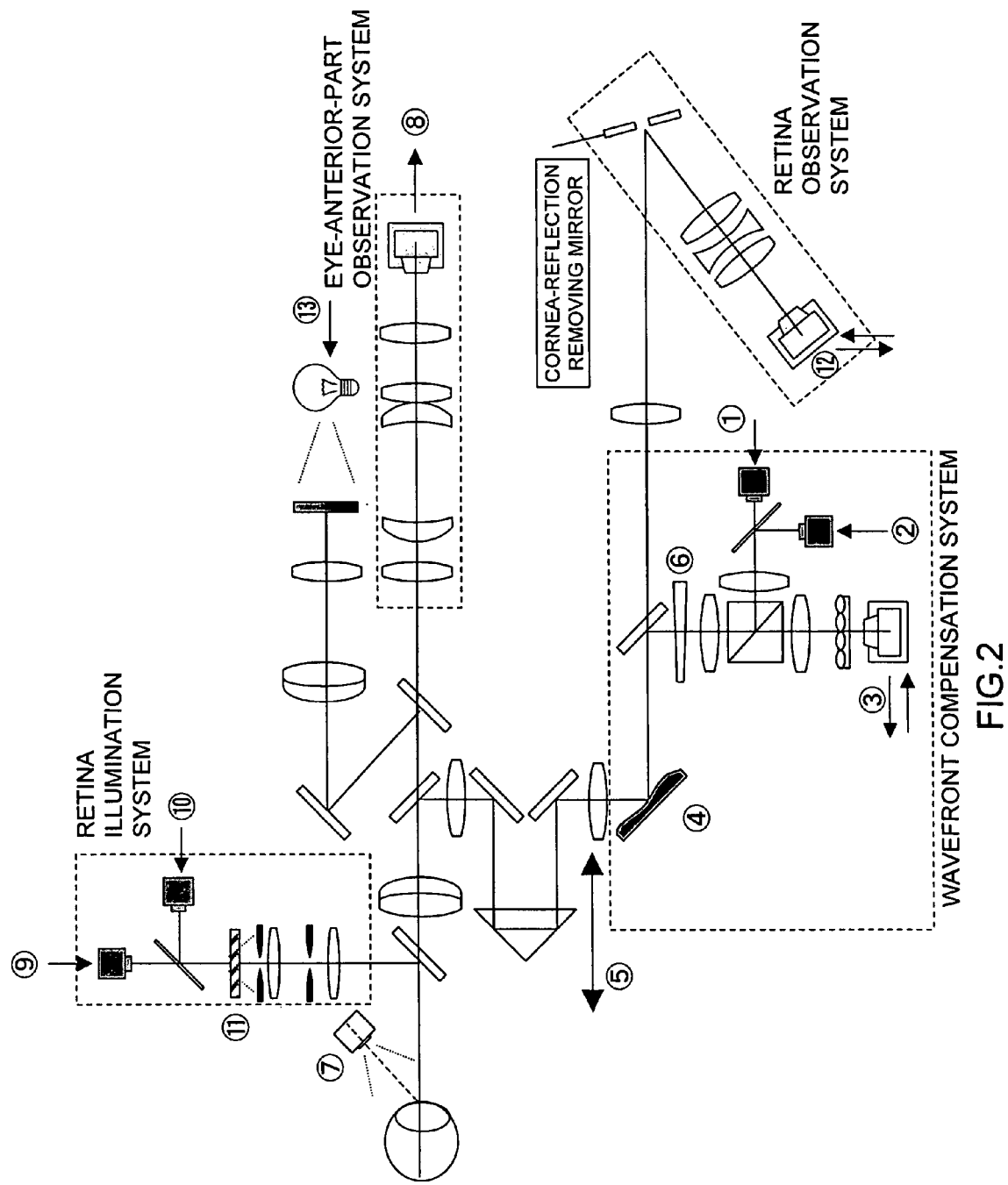
FIG. 2 is a view showing signals in the embodiment.
Figure 3:
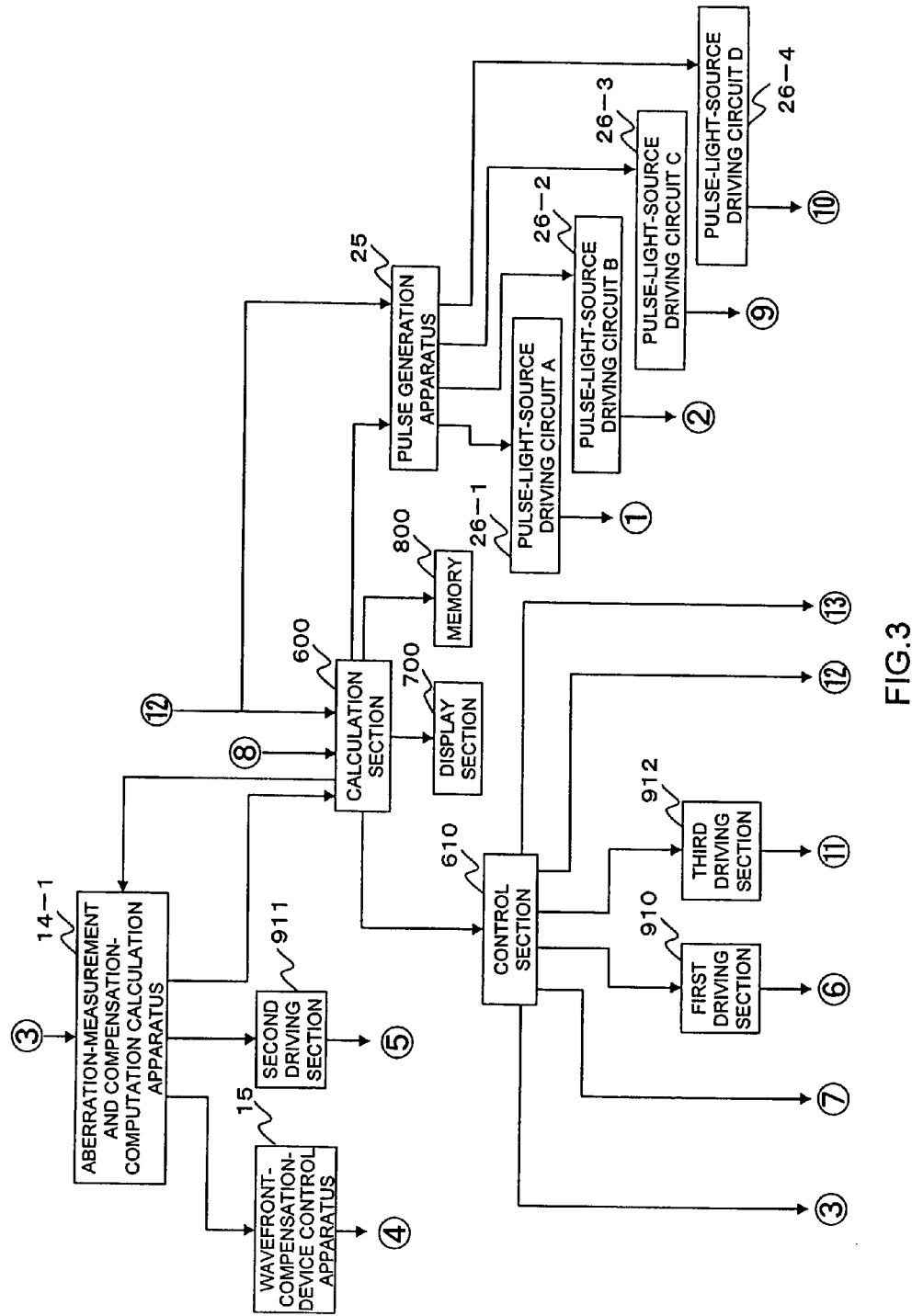
FIG. 3 is a block diagram of an electrical system in the embodiment.

FIG. 3 is a block diagram of an electrical system of the ophthalmologic imaging apparatus. FIG. 2 is a view showing signals in this embodiment.

In the structure of the electrical system of the ophthalmologic imaging apparatus, a calculation section 600, a control section 610, a display section 700, a memory 800, a first driving section 910, a second driving section 911, and a third driving section 912 are provided. The ophthalmologic imaging apparatus may further include an input section. As the input section, a pointing device for specifying a button, an icon, a position, an area, and others displayed on the display section 700, or a keyboard for inputting various types of data can be provided.

The calculation section 600 receives a second signal (12) from the first light-receiving section 32, a signal (8) from the eye-anterior-part observation system 4, and a signal from the calculation apparatus 14-1.

For example, the calculation section 600 receives a signal (8) from the eye-anterior-part observation system 4 and performs, for example, alignment adjustment. The calculation section 600 outputs signals corresponding to these processes, or other signals and data to the control section 610, which controls an electrical driving system, the display section 700, the memory 800, the calculation apparatus 14-1, and the pulse generation apparatus 25, if necessary.

The control section 610 controls turning on and off of the third light-source section 51, and the eye-anterior-part illumination light source 45, and controls the first driving section 910 and the third driving section 912 according to control signals sent from the calculation section 600. For example, the control section 610 outputs a signal (3) to the second light-receiving section 13, a signal (7) to the eye-anterior-part illumination light source 45, a signal (12) to the first light-receiving section 32, a signal (13) to the third light-source section 51, and further signals to the first driving section 910 and the third driving section 912, according to signals corresponding to calculation results in the calculation section 600.

The aberration-measurement and compensation-computation calculation apparatus 14-1 receives a first signal (3) from the second light-receiving section 13. According to the received signal, the calculation apparatus 14-1 calculates optical characteristics of the eye under measurement 60, such as aberrations and the amount of aberrations, and the amount of compensation used by the wavefront compensation device 71 for compensation. The calculation apparatus 14-1 outputs signals corresponding to these calculation results, or other signals and data to the calculation section 600, the wavefront-compensation-device control apparatus 15, and the second driving section 911, if necessary. The calculation apparatus 14-1 may be included in the calculation section 600. A signal may be input to the second driving section 911 through the control section 610.

The wavefront-compensation-device control apparatus 15 outputs a signal (3) according to the signal received from the calculation apparatus 14-1 to control the wavefront compensation device 17 so as to compensate for aberrations.

The pulse generation apparatus 25 receives a signal from the calculation section 600 and the signal (12) from the first light-receiving section 32. The pulse generation apparatus 25 generates pulses according to the received signals. The pulse generation apparatus 25 outputs signals corresponding to the generated pulses, or other signals and data to the pulse-light-source driving circuit A 26-1 to the pulse-light-source driving circuit D 26-4. According to the signals received from the pulse generation apparatus 25, the pulse-light-source driving circuit A 26-1 outputs a signal (1) to the first wavefront-measurement light source A 17-1, the pulse-light-source driving circuit B 26-2 outputs a signal (2) to the second wavefront-measurement light source B 17-2, the pulse-light-source driving circuit C 26-3 outputs a signal (9) to the first retina illumination light source A 21-1, and the pulse-light-source driving circuit D 26-4 outputs a signal (10) to the second retina illumination light source B 17-2.

The display section 700 displays an imaging result (a retinal image and others). The memory 800 stores measured aberrations, a captured image and time, settings such as predetermined exposure periods "$t_h$" and "$t_g$" for the first light-receiving section 32 and the second light-receiving section 13 and the number of measured images P, and others, if necessary. The calculation section 600 reads data from the memory 800 or writes data into the memory 800, if necessary.

The first driving section 910 outputs a signal (6) at least during the operation of the retina image sensor 32 to rotate a rotary prism 16. The second driving section 911, for example, outputs a signal (5) to drive movement means for the moving prism 72 to move the moving prism 72 along the optical axis. The third driving section 912, for example, outputs a signal (11) to rotate the rotating diffusion plate 24 at high speed.

4. Aberration Measurement

Next, an aberration measurement (a Zernike analysis) will be described. A generally known method of calculating Zernike coefficients $C_i^{2j-i}$ from Zernike polynomials will be described. The Zernike coefficients $C_i^{2j-i}$ are important parameters for grasping the optical characteristic of the subject eye 60 on the basis of inclination angles of the light fluxes obtained by the first light receiving part 13 through the conversion member, for example Hartmann plate.

Wavefront aberrations W(X, Y) of the subject eye 60 are expressed using the Zernike coefficients $C_i^{2j-i}$ and the Zernike polynomials $Z_i^{2j-i}$ by the following expression.

$$W(X, Y) = \sum_{i=0}^{n} \sum_{j=0}^{i} c_i^{2j-i} Z_i^{2j-i}(X, Y)$$

Where, (X, Y) denotes vertical and horizontal coordinates of the Hartmann plate.

Besides, with respect to the wavefront aberrations W(X, Y), when the horizontal and vertical coordinates of the second light receiving part 13 are denoted by (x, y), a distance between the Hartmann plate and the second light receiving part 13 is denoted by f, and a movement distance of a point image received by the second light receiving part 13 is denoted by (Δx, Δy), the following expression is established.

$$\frac{\partial W(X, Y)}{\partial X} = \frac{\Delta x}{f}$$

$$\frac{\partial W(X, Y)}{\partial Y} = \frac{\Delta y}{f}$$

Where, the Zernike polynomials $Z_i^{2j-i}$ are expressed by the following numerical expressions. (More specifically expressions, for example, see JP-A-2002-209854.)

$$Z_n^m = R_n^m(r) \begin{Bmatrix} \sin \\ \cos \end{Bmatrix} \{m\theta\}$$

$$m > 0 \quad \sin$$
$$m \leq 0 \quad \cos$$

$$R_n^m(r) = \sum_{S=0}^{(n-m)/2} (-1)^S \frac{(n-S)!}{S!\left\{\frac{1}{2}(n-m)-S\right\}!\left\{\frac{1}{2}(n+m)-S\right\}!} r^n$$

Incidentally, with respect to the Zernike coefficients $C_i^{2j-i}$, specific values can be obtained by minimizing the squared error expressed by the following numerical expression.

$$S(x) = \sum_{i=1}^{data\ number} \left[ \left\{ \frac{\partial W(X_i, Y_i)}{\partial X} - \frac{\Delta x_i}{f} \right\}^2 + \left\{ \frac{\partial W(X_i, Y_i)}{\partial Y} - \frac{\Delta y_i}{f} \right\}^2 \right]$$

Where, W(X, Y): wavefront aberrations, (X, Y): Hartmann plate coordinates, (Δx, Δy): a movement distance of a point image received by the second light receiving part 13, f: a distance between the Hartmann plate and the second light receiving part 13.

The calculation apparatus 14-1 calculates the Zernike coefficients $C_i^{2j-i}$, and uses this to obtain eye optical characteristics such as spherical aberrations, coma aberrations, and astigmatism aberrations. The calculation apparatus 14-1 calculates aberration quantities $RMS_i^{2j-i}$ using the Zernike coefficients $C_i^{2j-i}$ by the following numerical expression.

$$RMS_i^{2j-i} = \sqrt{\frac{\varepsilon_i^{2j-i}}{2(i+1)}} c_i^{2j-i}$$

$$(\varepsilon_i^{2j-i} = 2(2j = i), \varepsilon_i^{2j-i} = 1(2j \neq i))$$

5. Operation

Figure 4:
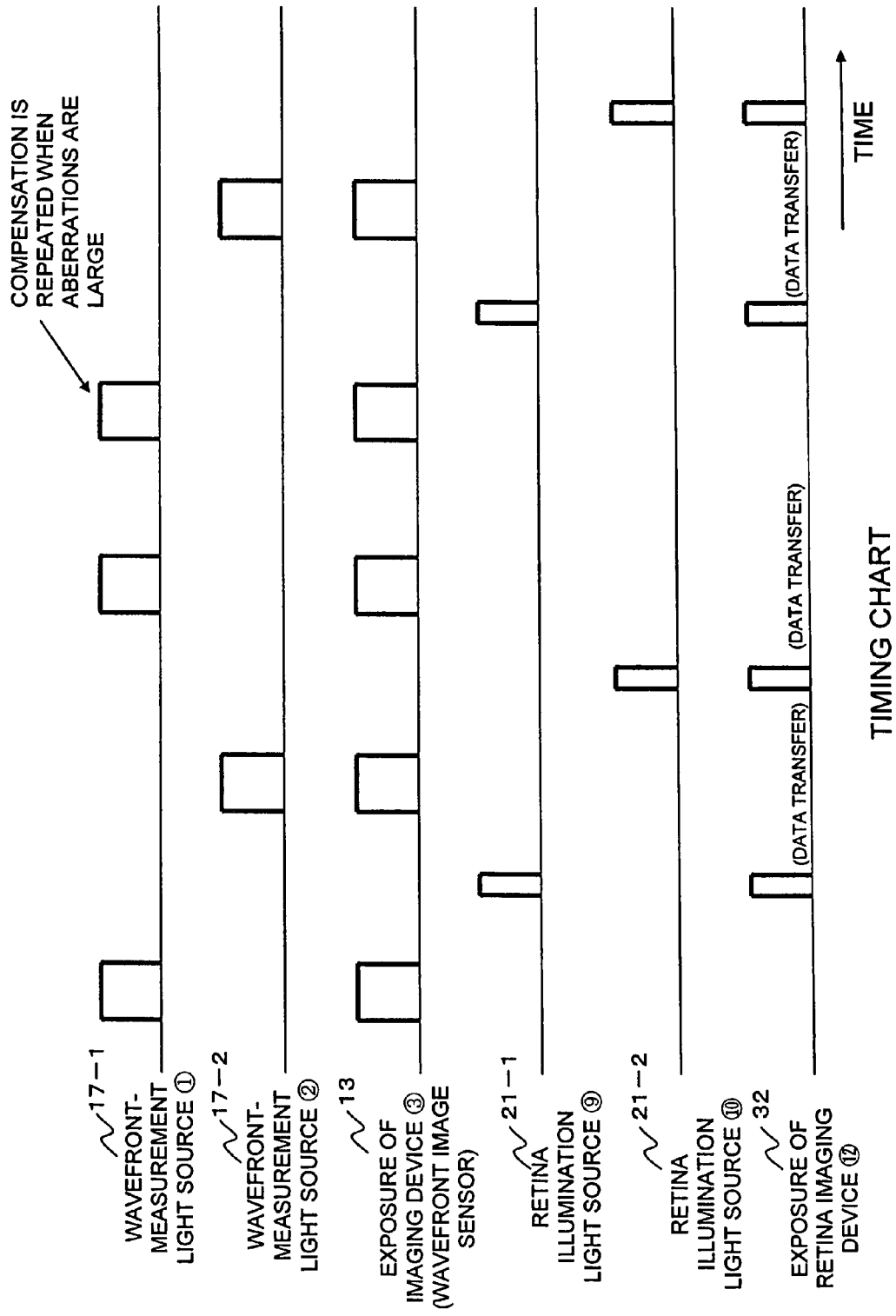
FIG. 4 is a timing chart of light sources and exposure of imaging devices.

FIG. 4 is a timing chart of the light emission of each light source and the exposure of each imaging device.

An outline of operation will be described first by referring to FIG. 4.

As shown in the figure, the first wavefront-measurement light source A 17-1 outputs light pulses having the first wavelength, and the wavefront image sensor 13 is exposed to light. The output and exposure timing can be synchronized. After the exposure of the wavefront image sensor 13, the calculation apparatus 14-1 reads a light-receiving signal of the wavefront image sensor 13 and measures aberrations according to the read light-receiving signal. The compensation optical system 70 performs compensation so as to cancel out the measured aberrations. After the aberration compensation, the first retina illumination light source A 21-1 outputs light pulses having the first wavelength, and the retina imaging sensor 32 is exposed to light. The output and exposure timing can be synchronized. After the exposure of the retina imaging sensor 32, the retina-imaging-device control apparatus 14-3 reads a light-receiving signal of the retina imaging sensor 32 and stores it in the memory 800.

During data transfer from the retina imaging device 32 and data storage into the memory 800, for example, the second wavefront-measurement light source B 17-2 outputs light pulses having the second wavelength, and the wavefront image sensor 13 is exposed to light. The output and exposure timing can be synchronized. The above operations may be performed after the data is stored in the memory 800. After the exposure of the wavefront image sensor 13, the calculation apparatus 14-1 reads a light-receiving signal of the wavefront image sensor 13 and measures aberrations according to the read light-receiving signal. The compensation optical system 70 performs compensation so as to cancel out the measured aberrations. After the aberration compensation, the second retina illumination light source B 21-2 outputs light pulses having the second wavelength, and the retina imaging sensor 32 is exposed to light. The output and exposure timing can be synchronized. After the exposure of the retina imaging sensor 32, the retina-imaging-device control apparatus 14-3 reads a light-receiving signal of the retina imaging sensor 32 and stores it in the memory 800.

During or after the transfer of the light-receiving signal, exposure for wavefront-aberration measurement at the first wavelength is performed in the same way as described above. If the aberration is larger than a threshold determined in advance, compensation is repeated. When the aberration becomes small, exposure of the retina imaging device 32 is started. At the timing described above, the processing is performed repeatedly until a predetermined number of images P are obtained.

Figure 5:
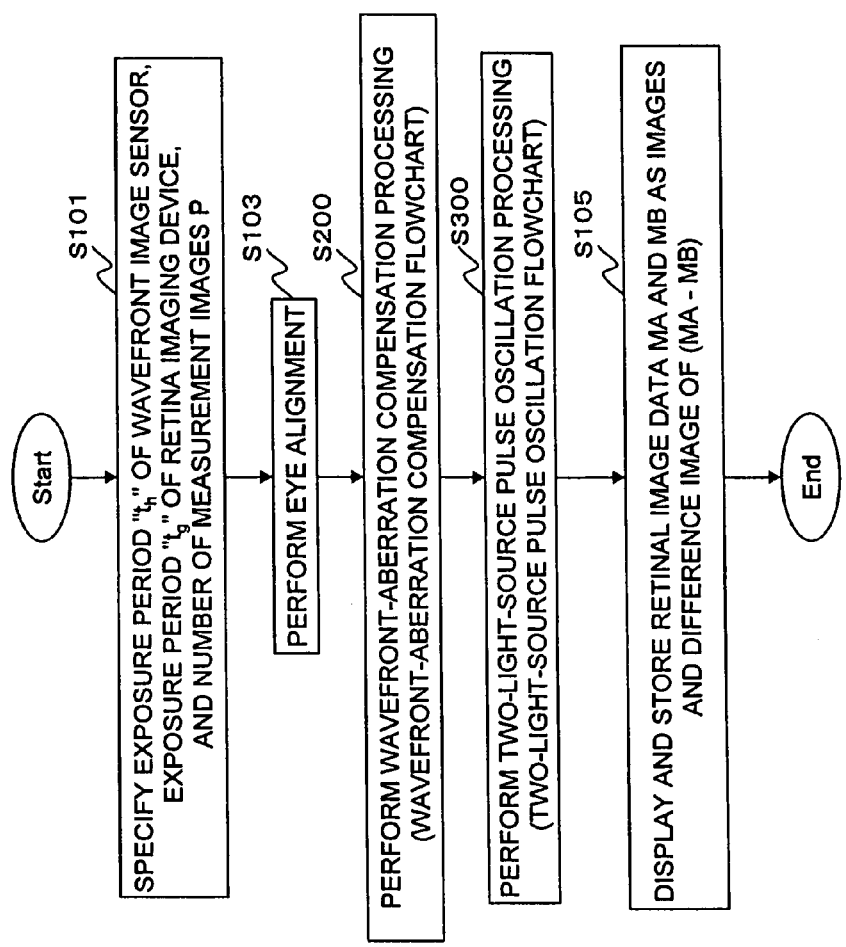
FIG. 5 is an overall flowchart in the embodiment.

FIG. 5 is an overall flowchart in the present embodiment.

The calculation section 600 first specifies the exposure period "$t_h$" of the wavefront image sensor 13, the exposure period "$t_g$" of the retina imaging sensor 32, and the number of measurement images P in step S101. The exposure period "$t_h$" of the wavefront image sensor 13, the exposure period "$t_g$" of the retina imaging sensor 32, and the number of measurement images P may be input from an appropriate input apparatus, or values thereof stored in advance in the memory 800 may be read.

Next, the calculation section 600 performs alignment of the eye under measurement in step S103. Another light source may be used to generate an alignment spot for eye alignment. In the present embodiment, for example, a light beam is projected to the eye anterior part, a light beam reflected from the eye anterior part is incident on the eye-anterior-part image sensor 41, and the operator moves the whole apparatus or the eye under measurement such that the center of the eye anterior part matches the origin of the eye-anterior-part image sensor 41 to perform eye alignment. Eye alignment may be performed at any appropriate timing.

Then, the calculation section 600 performs wavefront-aberration compensation processing for the eye under measurement in step S200. For example, the calculation apparatus 14-1 measures aberration according to the light-receiving signal of the wavefront image sensor 13 and uses the compensation optical system 70 to perform compensation so as to cancel out the measured aberration. Details of the wavefront-aberration compensation processing will be described later by referring to a wavefront-aberration compensation flowchart. The wavefront-aberration compensation processing, performed in step S200, may be omitted here but executed in two-light-source pulse oscillation processing, described later.

Then, the calculation section 600 performs the two-light-source pulse oscillation processing in step S300. Details of the two-light-source pulse oscillation processing will be described later with reference to a two-light-source pulse oscillation flowchart. For example, the calculation section 600 obtains retinal image data MA corresponding to pulse light having the first wavelength and retinal image data MB corresponding to pulse light having the second wavelength, and stores them in the memory 800.

The calculation section 600 reads the image data MA and MB, obtained in the two-light-source pulse oscillation processing, from the memory 800 and displays on the display section 700 as images in step S105. The calculation section 600 also obtains a difference image (MA−MB) of the image data and displays it on the display section 700. The calculation section 600 may store necessary data in the memory 800.

Figure 6:
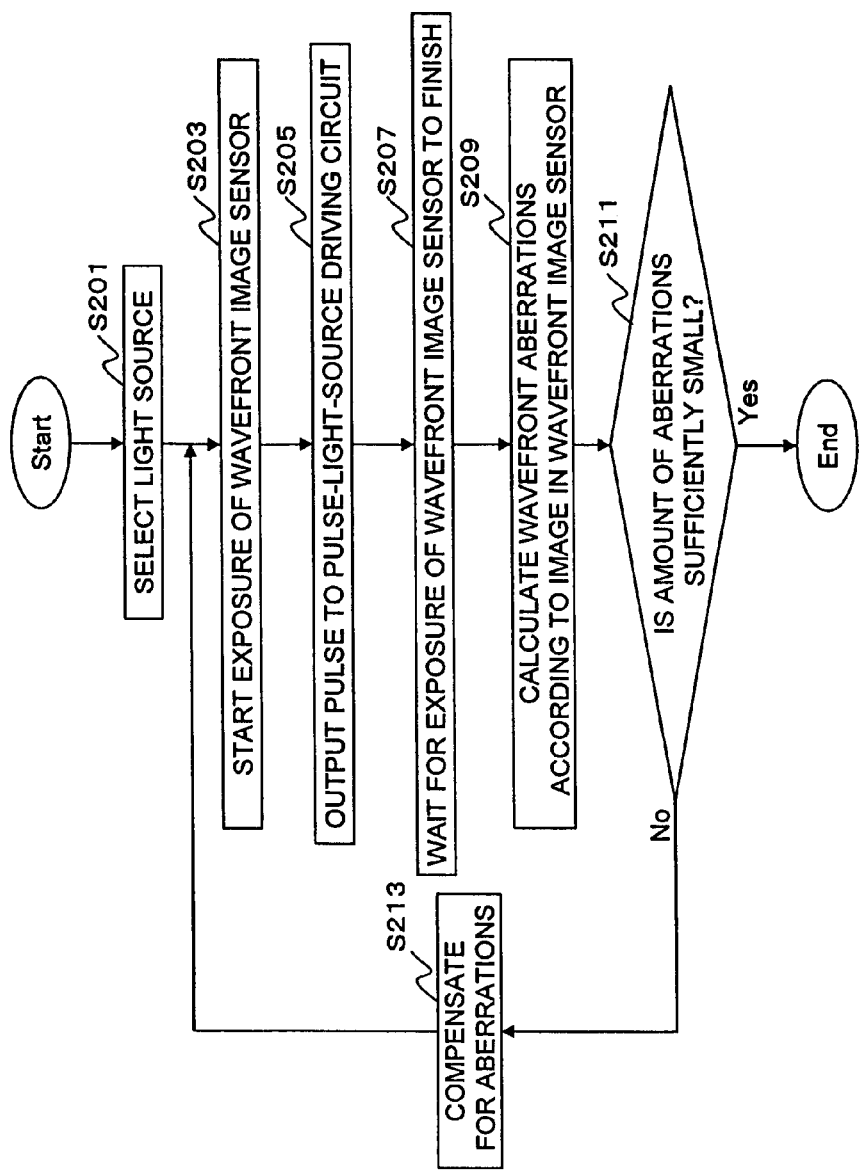
FIG. 6 is a flowchart of wavefront-aberration compensation processing.

FIG. 6 is the wavefront-aberration compensation flowchart, which is a detailed flowchart of step S200, described above.

The calculation section 600 first selects either the first wavefront-measurement light source A 17-1 or the second wavefront-measurement light source B 17-2 in step S201. For example, the operator may input the selection from the input section, or a light source used for first capturing in the two-light-source pulse oscillation processing may be determined in advance and selected. The calculation section 600 uses the control section 610 to start exposure of the wavefront image sensor 13 in step S203. In step S205, the pulse generation apparatus 25, for example, generates a pulse corresponding to the specified exposure period "$t_h$" of the wavefront image sensor 13 and outputs the generated pulse to the pulse-light-source driving circuit A 26-1 or the pulse-light-source driving circuit B 26-1, corresponding to the light source 17-1 or the light source 17-2, respectively, selected in step S201. The wavefront-measurement light source 17-1 or 17-2 selected is controlled by the pulse-light-source driving circuit A 26-1 or B 26-2 to emit pulsed light corresponding to the received pulse.

The calculation section 600 waits for the exposure of the wavefront image sensor 13 to finish in step S207. For example, the calculation section 600 waits for the specified exposure period "$t_h$". After the exposure of the wavefront image sensor 13 finishes, the calculation apparatus 14-1 reads an image from the wavefront image sensor 13 and performs wavefront-aberration calculation processing according to the read image in step S209. For example, the calculation apparatus 14-1 calculates the amount R of the aberration of the eye according to the measurement results (Zernike coefficients $c_i^{2j-i}$, for example) of the aberration measurement and stores the calculation result in the memory 800. The amount R of aberration can be calculated as the standard deviation of the measurement results from an ideal wavefront (aplanatic state). For example, the amount R of aberration can be obtained in a simplified manner by the use of the Zernike coefficients by the following expression. In the expression, "order" means the order of the Zernike coefficients, and "order" is, for example, set to a value such as 4 or 6.

$$R = \sqrt{\sum_{i=0}^{order} \sum_{j=0}^{i} \frac{\varepsilon_i^{2j-i}}{2(i+1)} (c_i^{2j-i})^2}$$

$$(\varepsilon_i^{2j-i} = 2(2j=i), \varepsilon_i^{2j-i} = 1(2j \neq i))$$

Next, the calculation apparatus 14-1 determines in step S211 whether the amount R of aberration is sufficiently small or not. For example, the calculation apparatus 14-1 determines whether the amount R of aberration is smaller than a threshold determined in advance. If the amount R of aberration is not sufficiently small in step S211, the calculation apparatus 14-1 performs an aberration compensation process in step S213. For example, the calculation apparatus 14-1 moves the movement prism 72 through the second driving section 911 and controls the wavefront compensation device 71 through the wavefront-compensation-device control apparatus 15 to perform compensation so as to cancel out the measured aberration. Then, the processing returns to step S203.

The calculation section 600 repeats the processes of steps S203 to S213 until the amount R of aberration becomes sufficiently small. When it is determined in step S211 that the amount R of aberration is sufficiently small, the calculation section 600 finishes the wavefront-aberration compensation processing.

Figure 7:
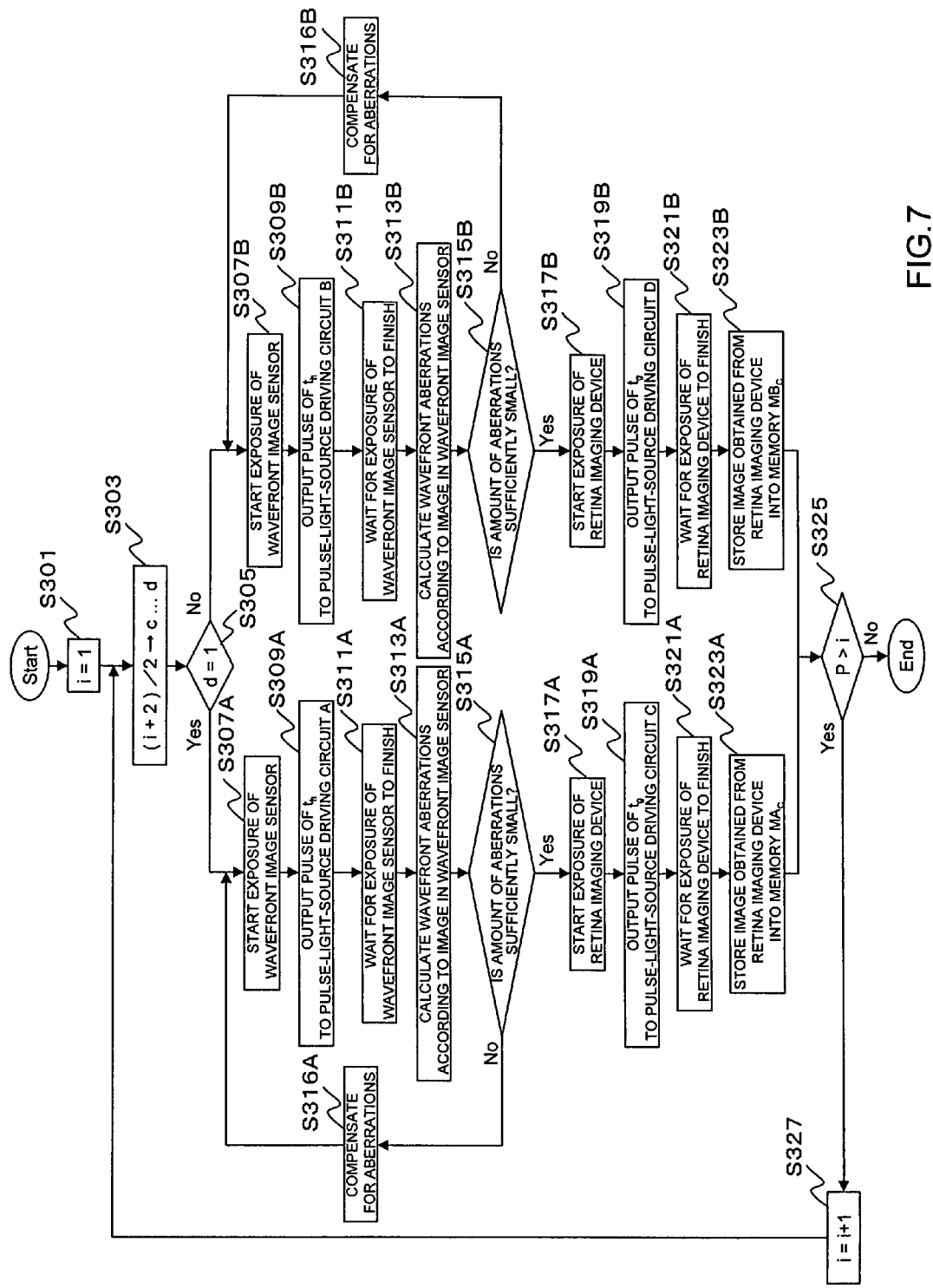
FIG. 7 is a flowchart of two-light-source pulse oscillation processing.

FIG. 7 is the two-light-source pulse oscillation flowchart, which is a detailed flowchart of step S300, described above.

The calculation section 600 first specifies an initial setting in step S301. For example, the calculation section 600 sets a parameter "i" to "1". The parameter "i" indicates, for example, the number of measurement images or the number of imaging operations. Next, the calculation section 600 determines in steps S303 and S305 which of the two different wavelengths is used for measurement. Here, as an example, the first wavelength and the second wavelength are alternately used. However, the selection of the wavelengths is not limited to this way of selection. In the present embodiment, as an example, (i+2)/2 is calculated in step S303; the quotient of the calculation is called "c" and the remainder is called "d"; when the remainder is "1" (d=1) (Yes in step S305), the processing proceeds to step S307A; and when the remainder is not "1" (No in step S305), the processing proceeds to step S307B. Any appropriate method other than that described above may be used in the determination process of which of the two different wavelengths is used for measurement.

In step S307A, the calculation section 600 uses the control section 610 to start the exposure of the wavefront image sensor 13. The pulse generation apparatus 25 generates a pulse corresponding to a specified exposure period of "$t_h$" seconds of the wavefront image sensor 13 and outputs the generated pulse to the pulse-light-source driving circuit A 26-1 in step S309A. The first wavefront-measurement light source A 17-1 emits pulsed light corresponding to the pulse generated in step S309A, under the control of the pulse-light-source driving circuit A 26-1.

The calculation section 600 waits for the exposure of the wavefront image sensor 13 to finish, in step S311A. For example, the calculation section 600 waits for an exposure period of "$t_h$" seconds, specified in step S101. After the exposure of the wavefront image sensor 13 finishes, the calculation apparatus 14-1 reads an image from the wavefront image sensor 13 and calculates wavefront aberration according to the read image, in step S313A. The wavefront aberration is calculated in the same way as in step S209 in the wavefront-aberration compensation flowchart, described above.

Next, the calculation apparatus 14-1 determines in step S315A whether the amount R of aberration is sufficiently small or not. For example, the calculation apparatus 14-1 determines whether the amount R of aberration is smaller than a threshold determined in advance. If the amount R of aberration is not sufficiently small in step S315A, the calculation apparatus 14-1 performs an aberration compensation process in step S316A. For example, the calculation apparatus 14-1 moves the movement prism 72 through the second driving section 911 and controls the wavefront compensation device 71 through the wavefront-compensation-device control apparatus 15 to perform compensation so as to cancel out the measured aberration. Then, the processing returns to step S307A.

When the amount R of aberration is sufficiently small in step S315A, the calculation section 600 uses the control section 610 to start the exposure of the retina imaging device 32 in step S317A. The pulse generation apparatus 25 generates a pulse corresponding to a specified exposure period of "$t_g$" seconds of the retina imaging device 32 and outputs the generated pulse to the pulse-light-source driving circuit C 26-3 in step S319A. The first retina illumination light source A 21-1 emits pulsed light corresponding to the pulse generated in step S319A, under the control of the pulse-light-source driving circuit C 26-3.

The calculation section 600 waits for the exposure of the retina imaging device 32 to finish, in step S321A. For example, the calculation section 600 waits for an exposure period of "$t_g$" seconds, specified in step S101. After the exposure finishes, the calculation section 600 reads an image from the retina imaging device 32 and stores it in the memory 800 as image data $MA_c$ in step S323A. For example, the data is stored in association with information that identifies the first wavelength. The time, data number, and others may be further stored. The quotient "c" in step S303 may be used as the data number.

The calculation section 600 determines in step S325 whether the parameter "i" is smaller than the number of measurement images P. In other words, the calculation section 600 determines whether the parameter "i" reaches the number of measurement images P. When the parameter "i" is smaller than P in step S325, the calculation section 600 increments the value of "i" (for example, i=i+1) in step S327, and the processing returns to step S303. In step S303, since "i" equals "2", the quotient "c" is "2" and the remainder "d" is "0". Therefore, it is determined in step S305 that "d" is not "1" (No in step S305), the processing proceeds to step S307B.

In step S307B, the calculation section 600 uses the control section 610 to start the exposure of the wavefront image sensor 13. The pulse generation apparatus 25 generates a pulse corresponding to a specified exposure period of "$t_h$" seconds of the wavefront image sensor 13 and outputs the generated pulse to the pulse-light-source driving circuit B 26-2 in step S309B. The second wavefront-measurement light source B 17-2 emits pulsed light corresponding to the pulse generated in step S309B, under the control of the pulse-light-source driving circuit B 26-2.

The calculation section 600 waits for the exposure of the wavefront image sensor 13 to finish, in step S311B. For example, the calculation section 600 waits for an exposure period of "$t_h$" seconds, specified in step S101. After the exposure of the wavefront image sensor 13 finishes, the calculation apparatus 14-1 reads an image from the wavefront image sensor 13 and calculates wavefront aberration according to the read image, in step S313B. The wavefront aberration is calculated in the same way as in step S209 in the wavefront-aberration compensation flowchart, described above.

Next, the calculation apparatus 14-1 determines in step S315B whether the amount R of aberration is sufficiently small or not. For example, the calculation apparatus 14-1 determines whether the amount R of aberration is smaller than a threshold determined in advance. If the amount R of aberration is not sufficiently small in step S315B, the calculation apparatus 14-1 performs an aberration compensation process in step S316B. For example, the calculation apparatus 14-1 moves the movement prism 72 through the second driving section 911 and controls the wavefront compensation device 71 through the wavefront-compensation-device control apparatus 15 to perform compensation so as to cancel out the measured aberration. Then, the processing returns to step S307B.

When the amount R of aberration is sufficiently small in step S315B, the calculation section 600 uses the control section 610 to start the exposure of the retina imaging device 32 in step S317B. The pulse generation apparatus 25 generates a pulse corresponding to a specified exposure period of "$t_g$" seconds of the retina imaging device 32 and outputs the generated pulse to the pulse-light-source driving circuit D 26-4 in step S319B. The second retina illumination light source B 21-2 emits pulsed light corresponding to the pulse generated in step S319B, under the control of the pulse-light-source driving circuit D 26-4.

The calculation section 600 waits for the exposure of the retina imaging device 32 to finish, in step S321B. For example, the calculation section 600 waits for an exposure period of "$t_g$" seconds, specified in step S101. After the exposure finishes, the calculation section 600 reads an image from the retina imaging device 32 and stores it in the memory 800 as image data $MB_c$ in step S323B. For example, the data is stored in association with information that identifies the second wavelength. The time, data number, and others may be further stored. The quotient "c" in step S303 may be used as the data number.

The processes of steps S307B to S316B may be performed during the transfer or the storage of the image in step S323A. In the same way, the processes of steps S307A to S316A may be performed during the transfer or the storage of the image in step S323B.

The calculation section 600 determines in step S325 in the same way as described above whether the parameter "i" is smaller than the number of measurement images P. In other words, the calculation section 600 determines whether the parameter "i" reaches the number of measurement images P. When the parameter "i" is smaller than P in step S325, the calculation section 600 increments the value of "i" (for example, i=i+1) in step S327, and the processing returns to step S303.

As described above, the calculation section 600 repeatedly performs the processes of steps S305 to S327. After the predetermined number of measurement images P are taken, it is determined in step S325 that the parameter "i" is not smaller than P, and the calculation section 600 terminates the two-light-source pulse oscillation processing.

In the flowchart described above, control is made such that the timing when the second illumination optical system 11 forms a point image on the retina differs from the timing when the first illumination optical system 2 illuminates the observation area. When the second illumination optical system 11 forms an point image on the retina at a position outside the observation area of the first illumination optical system 2, noise is prevented from coming from the wavefront-measurement light source. In the above-described processing, two light sources are used. The processing needs to be modified appropriately if three light sources or n (n: integer) light sources are used.

Figure 8B:
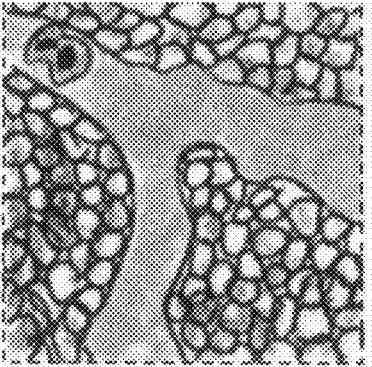
FIG. 8A to FIG. 8C show display examples of results in the embodiment.
Figure 8C:
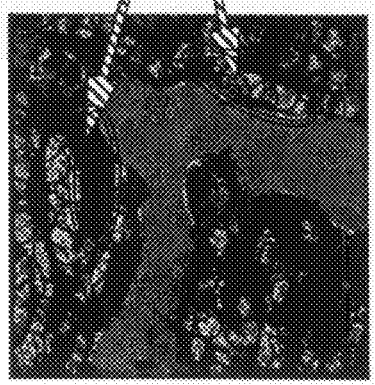
Figure 8A:
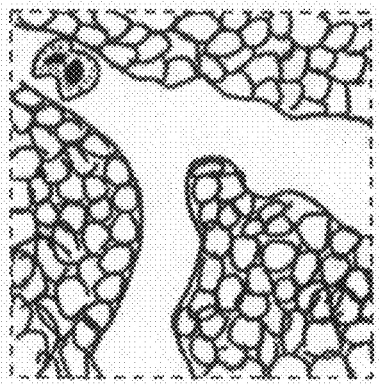

FIG. 8A to FIG. 8C show display examples of results in the present embodiment. In FIG. 8A shows a retinal image obtained with light having the first wavelength (wavelength A, for example, 532 nm); FIG. 8B shows a retinal image obtained with light having the second wavelength (wavelength B, for example, 635 nm); and FIG. 8C shows a difference image of the retinal images obtained with the wavelengths A and B.

Cone cells are located among cells that are sensitive to light in the retina of an human eye and are divided into L cone cells, M cone cells, and S cone cells by differences in wavelength sensitivity. Roughly speaking, the L cone cells react strongly to red (long wavelength), the M cone cells react strongly to green (intermediate wavelength), and the S cone cells strongly react to blue (short wavelength). These reactions are processed by the brain to determine the color.

Therefore, the type of cone cells differs depending on the wavelength of light incident on an eye. When an eye under measurement cannot distinguish between red and green due to the distribution of the types of cone cells, for example, the cause can be identified by taking and displaying images obtained with light beams having different wavelengths and by comparing the images with those of a normal eye.

Since the images shown in FIG. 8A and FIG. 8B were taken within a very short period of time, they can be deemed to be retinal images taken almost at the same time with light having different wavelengths. From those images, the difference image shown in FIG. 8C can be obtained, allowing spectroscopic measurement. It is understood from spectroscopic measurement that cells react differently depending on the wavelengths.

The difference image shown in FIG. 8C can be used for observing hemoglobin. Active portions can be displayed in detail from FIG. 8C by using oxygen saturation. Portions showing no change (for example, black portions) are not made active, which indicates that cells therein do not function any more. When the difference image obtained by this embodiment is used for artificial-retina inspection, the image shows portions where a function does not perform well.

Figure 9:
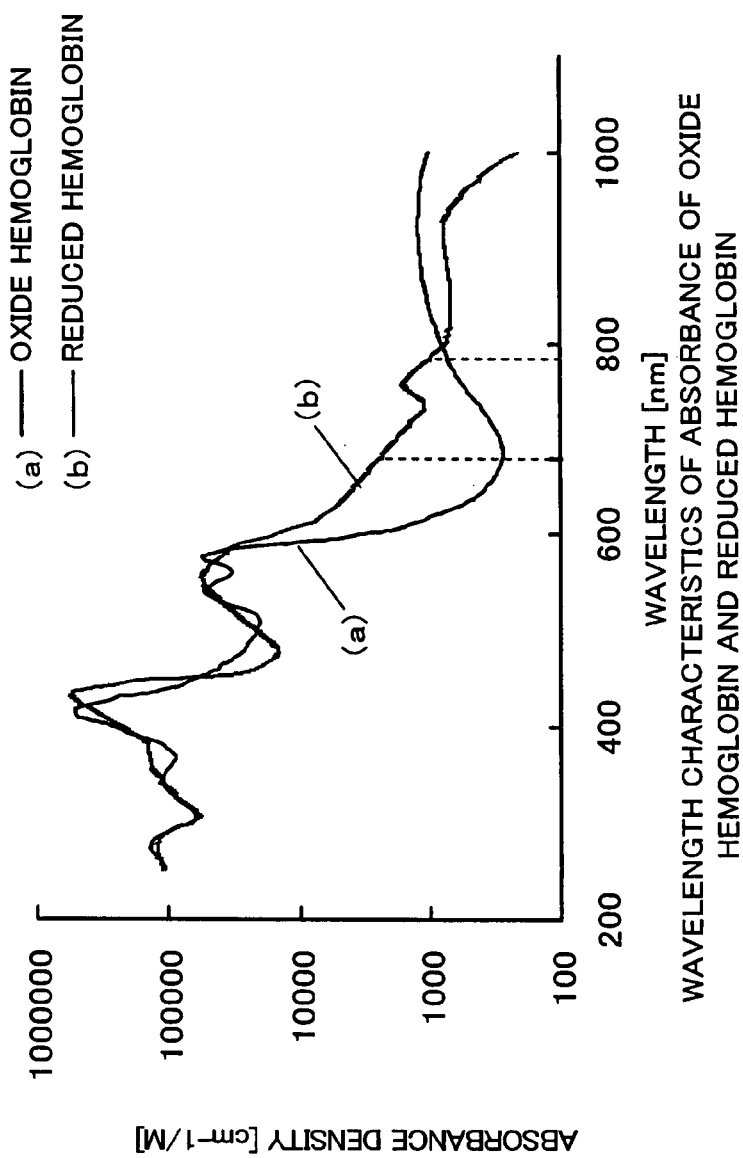
FIG. 9 is a view showing wavelength characteristics of the levels of absorbance of oxide hemoglobin and reduced hemoglobin.

FIG. 9 is a view showing wavelength characteristics of the levels of absorption of oxide hemoglobin and reduced hemoglobin. The horizontal axis indicates the wavelength and the vertical axis indicates the absorbance density.

For example, images are taken respectively with light having wavelengths of 700 nm and 800 nm, and called an image A and an image B. Since oxide hemoglobin (a) and reduced hemoglobin (b) have a difference in optical absorbance depending on wavelengths, when a difference in pixel value at a position between the image A and the image B is obtained, it is determined whether oxide hemoglobin or reduced hemoglobin exists at the position. For example, as shown in FIG. 9, when a comparison in absorbance density is made between a wavelength of 700 nm and a wavelength of 800 nm, it can be predicted that there are much oxide hemoglobin at areas where the absorbance density increases and that there are much reduced hemoglobin at areas where the absorbance density decreases.

When hemoglobin has a high absorbance density, the retina imaging device 32 receives a small amount of light. Therefore, a pixel value is small at a position where such hemoglobin exists. When hemoglobin has a low absorbance density, the retina imaging device 32 receives a large amount of light. Therefore, a pixel value is large at a position where such hemoglobin exists. When the difference between the image A and the image B is obtained, for example, pixel values at areas other than those where oxide hemoglobin or reduced hemoglobin exists are cancelled out, and the areas where oxide hemoglobin or reduced hemoglobin exists are extracted. As an example benefit of using different wavelengths, oxide hemoglobin and reduced hemoglobin have been taken. The present invention is not limited to this case. It can be applied to any appropriate cases.

6. Modification

Outline

As a modification of the above-described embodiment, three light sources, red (R), green (G), and blue (B) light sources, can be used to obtain a color retinal image. For example, a blue LED (having a wavelength of 430 nm), a green LED (having a wavelength of 565 nm), and a red LED (having a wavelength of 700 nm) are used as light sources; and images obtained respectively with the light sources are combined as blue information, green information, and red information to generate a color retinal image.

Optical Arrangement

Figure 10:
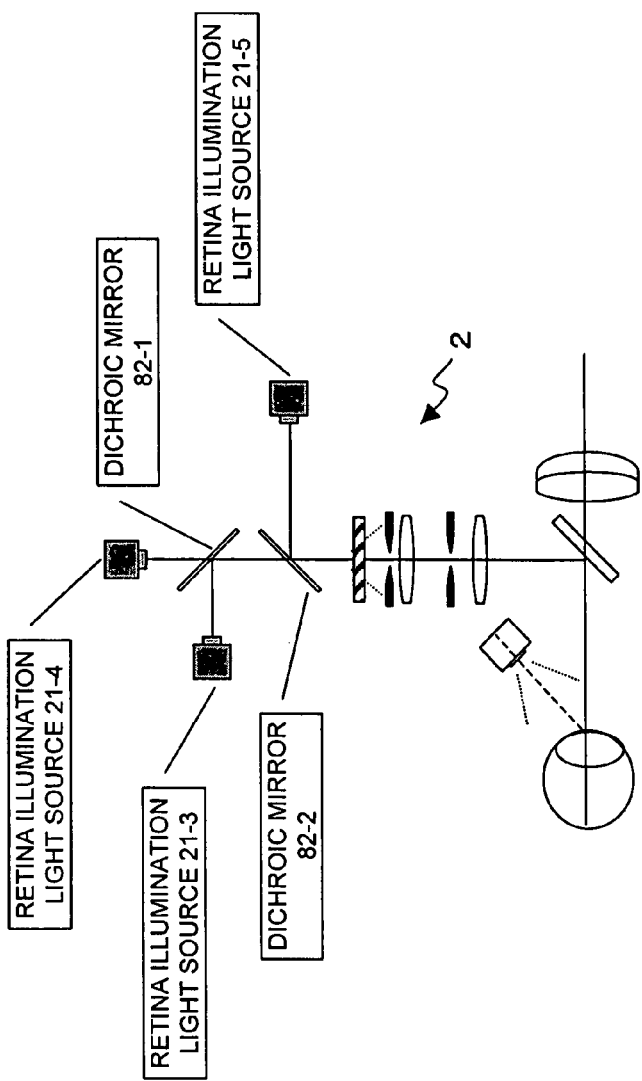
FIG. 10 is a view showing an optical arrangement in which three (three-wavelength) retina illumination light sources are used.

FIG. 10 is a view showing a part of optical arrangement in which three (three-wavelength) retina illumination light sources are used.

In the figure, only a first illumination optical system 2 is shown, but a second illumination optical system 11 also uses three light sources in the same way. Since the other structures are the same as those shown in FIG. 1, a description thereof is omitted.

The first illumination optical system (retina illumination system) 2 includes, for example, a first light source section (for example, a retina illumination light source 21-3, a retina illumination light source 21-4, and a retina illumination light source 21-5), a dichroic mirror section (for example, a dichroic mirror 82-1 and a dichroic mirror 82-2).

As the retina illumination light source 21-3, an LED having a third wavelength (for example, a wavelength of 430 nm, blue) can be used. As the retina illumination light source 21-4, an LED having a fourth wavelength (for example, a wavelength of 565 nm, green) can be used. As the retina illumination light source 21-5, an LED having a fifth wavelength (for example, a wavelength of 700 nm, red) can be used.

In this modification, three wavefront-measurement light sources 17 are used in the same way as the retina illumination light sources 21. The wavefront-measurement light sources 17 have the same wavelengths as the corresponding retina illumination light sources 21. For example, one of the light sources used for wavefront measurement has the third wavelength as the retina illumination light source 21-3. In the same way, the other two light sources used for wavefront measurement have the fourth wavelength and the fifth wavelength. There is also provided a plurality of pulse-light-source driving circuits 26 corresponding to the retina illumination light sources 21 and the wavefront-measurement light sources 17.

As the dichroic mirror 82-1, a hot mirror that reflects light having the third wavelength (for example, 430 nm) and that passes light having the fourth wavelength (for example, 565 nm) can be used. As the dichroic mirror 82-2, a hot mirror that reflects light having the fifth wavelength (for example, 700 nm) and that passes light having the third wavelength (for example, 430 nm) and light having the fourth wavelength (for example, 565 nm) can be used. The same dichroic mirrors are also used in a wavefront compensation system 1. Since the other structures are the same as those in the above-described embodiment, a description thereof is omitted.

In the same way as in the above-described embodiment, the wavefront is compensated at each wavelength and a retinal image is obtained with light having each wavelength. For example, a retina-imaging-device control apparatus 14-3 combines retinal images obtained with light beams having these three wavelengths to acquire a color retinal image. The acquired color retinal image is displayed on a display section 700 and/or stored in a memory 800.

The present invention can be used, for example, for retinal-image imaging apparatuses in ophthalmology.

What is claimed is:

1. An ophthalmologic imaging apparatus comprising:
a first light source section comprising a first light source for emitting a light beam having a first wavelength and a second light source for emitting a light beam having a second wavelength both for illuminating a desired observation area on a retina of an eye under measurement;
a second light source section comprising a third light source for projecting a light beam having the first wavelength on the retina as an almost point image and a fourth light source for projecting a light beam having the second wavelength on the retina as an almost point image;
a first illumination optical system for illuminating the observation area on the retina, with a first light beam emitted from the first light source section;
a second illumination optical system for projecting a second light beam emitted from the second light source section on the retina as an almost point image;
an aberration compensation section for applying compensation to a first reflected light beam obtained when the first light beam is reflected by the retina and a second reflected light beam obtained when the second light beam is reflected by the retina so as to cancel out aberrations that include at least high-order aberrations, according to aberrations measured at the first wavelength and the second wavelength;
an aberration measurement section comprising a second light-receiving section for receiving the second reflected light beam which aberrations have been compensated for by the aberration compensation section, through a dividing means for dividing into at least 17 beams, the aberration measurement section measuring aberrations of the second reflected light beam at the first wavelength or the second wavelength according to a light-receiving signal of the second light-receiving section;
a first light-receiving section for receiving the first reflected light beam coming from the retina, which aberrations have been compensated for by the aberration compensation section; and
a light-receiving optical system for forming a retinal image on the first light-receiving section with the first reflected light beam coming from the retina through the aberration compensation section,
wherein,
after a light beam is emitted from the third light source and aberrations at the first wavelength are compensated for by the aberration compensation section, a first retinal image formed through the aberration compensation section on the first light-receiving section by a light beam having the first wavelength coming from the first light source is obtained; and
after a light beam is emitted from the fourth light source and aberrations at the second wavelength are compensated for by the aberration compensation section, a second retinal image formed through the aberration compensation section on the first light-receiving section by a light beam having the second wavelength coming from the second light source is obtained.

2. An ophthalmologic imaging apparatus according to claim 1, wherein
the second illumination optical system forms the almost point image on the retina at a position outside the observation area of the first illumination optical system.

3. An ophthalmologic imaging apparatus according to claim 1, wherein
the second light source section and the second illumination optical system form the almost point image on the retina at timing different from timing when the first light source section and the first illumination optical system illuminate the observation area.

4. An ophthalmologic imaging apparatus according to claim 1, further comprising
a calculation section for reading the retinal image data formed on the first light-receiving section, and for storing the retinal image in a storage section or for displaying the retinal image on a display section,
wherein
while the calculation section reads the first retinal image formed on the first light-receiving section by a light beam coming from the first light source, and stores or displays the first retinal image, the fourth light source emits a light beam having the second wavelength and aberrations at the second wavelength are compensated for.

5. An ophthalmologic imaging apparatus according to claim 4, wherein
when aberrations at the second wavelength are compensated for by the aberration compensation section with the light beam having the second wavelength, coming from the fourth light source, and the calculation section finishes reading the first retinal image from the first light-receiving section, the second light source emits a light beam having the second wavelength and the second retinal image is obtained from the first light-receiving section.

6. An ophthalmologic imaging apparatus according to claim 1, further comprising:
a calculation section for obtaining a difference image between the first retinal image obtained and the second retinal image obtained; and
a display section for displaying one of or plurality of the first retinal image obtained, the second retinal image obtained, and the difference image obtained.

7. An ophthalmologic imaging apparatus according to claim 1, wherein the first light source and the second light source emit pulsed light corresponding to an exposure period of time of the first light-receiving section.

8. An ophthalmologic imaging apparatus according to claim 1, wherein
the third light source and the fourth light source emit pulsed light corresponding to an exposure period of time of the second light-receiving section.

9. An ophthalmologic imaging apparatus according to claim 1, further comprising
a calculation section for controlling the timing of light emission of the first to fourth light sources and the timing of exposure of the first and second light-receiving sections.

10. An ophthalmologic imaging apparatus according to claim 1, wherein
the first light source section further comprises a fifth light source for emitting a light beam having a third wavelength for illuminating the desired observation area on the retina of the eye under measurement;

the second light source section further comprises a sixth light source for projecting a light beam having the third wavelength on the retina as an almost point image;

the first to third wavelengths are wavelengths corresponding to three primary colors;

after a light beam is emitted from the sixth light source and aberrations at the third wavelength are compensated for by the aberration compensation section, a third retinal image formed on the first light-receiving section through the aberration compensation section by a light beam coming from the fifth light source is obtained; and a color retinal image is obtained based on the first to third retinal images obtained.

* * * * *